United States Patent [19]

Nakagawa et al.

[11] Patent Number: 5,202,266
[45] Date of Patent: Apr. 13, 1993

[54] 25-HYDROXY VITAMIN $D_3$ DERIVATIVES, PROCESS FOR THEIR PRODUCTION, AND ASSAY METHOD USING THE SAME

[75] Inventors: Nobuaki Nakagawa; Shigeru Ikuta; Miyuki Tanabe, all of Shizuoka, Japan

[73] Assignee: Asahi Kasei Kogyo Kabushiki Kaisha, Osaka, Japan

[21] Appl. No.: 733,628

[22] Filed: Jul. 22, 1991

Related U.S. Application Data

[62] Division of Ser. No. 258,017, Oct. 14, 1988, Pat. No. 5,075,465.

[30] Foreign Application Priority Data

Oct. 14, 1987 [JP] Japan .................................. 62-258584
Aug. 25, 1988 [JP] Japan .................................. 63-211364

[51] Int. Cl.$^5$ ........................................ G01N 33/537
[52] U.S. Cl. .................................... 436/501; 436/542; 436/815
[58] Field of Search ...................... 436/542, 501, 815

[56] References Cited

U.S. PATENT DOCUMENTS

| | | | |
|---|---|---|---|
| 4,119,647 | 10/1978 | Liebman et al. | 552/653 |
| 4,225,525 | 9/1980 | Baggiolini et al. | 549/511 |
| 4,269,777 | 5/1981 | De Luca et al. | 514/167 |
| 4,424,161 | 1/1984 | Holick | 552/653 |
| 4,585,741 | 4/1986 | Clevinger et al. | 436/542 |
| 4,816,417 | 3/1989 | De Luca et al. | 436/542 |
| 5,064,770 | 11/1991 | De Luca et al. | 436/542 |

FOREIGN PATENT DOCUMENTS

| | | |
|---|---|---|
| 363211 | 4/1990 | European Pat. Off. . |
| 2376864 | 8/1978 | France . |
| 55-47653 | 4/1980 | Japan . |
| 56-500538 | 4/1981 | Japan . |
| 58-92656 | 6/1983 | Japan . |
| 59-148775 | 8/1984 | Japan . |
| 60-163859 | 8/1985 | Japan . |
| 1589921 | 5/1981 | United Kingdom . |
| 80/02562 | 11/1980 | World Int. Prop. O. . |

OTHER PUBLICATIONS

Yamamoto et al., J. of Biochem., vol. 98, No. 4 (1985) pp. 991-998, "Monoclonal Antibody for Calcitriol ($\alpha$, 25-Dihydroxyvitamin $D_3$)".
Vitamin, 55(12), (1981) pp. 595-605.
M. Tanabe et al., J. Nutr. Sci. Vitaminol. (Tokyo), 37(2), 139-47 (1991).

*Primary Examiner*—Mary E. Ceperley
*Attorney, Agent, or Firm*—Young & Thompson

[57] ABSTRACT

A novel 25-hydroxy vitamin $D_3$ amino acid derivative of the formula

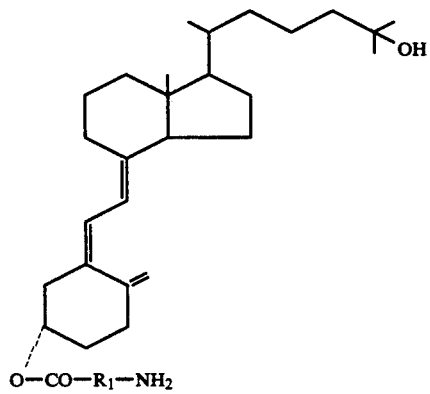

wherein $R_1$ is $C_{1-10}$ alkylene, is produced by removing a protective group for the amino group, e.g. 9-fluorenylmethyloxycarbonyl, in the presence of a base in an inert solvent. A radioisotope iodine-labeled residue is then attached to the amino group to produce a derivative useful in the assay of 25-hydroxy vitamin $D_3$ in a specimen.

4 Claims, 6 Drawing Sheets

$\dfrac{B - B_L}{B_0 - B_L} \times 100$ (‰)

25-OHD₃ (pg/T)

— ▲ — n = 1
— ● — n = 2
— ■ — n = 3

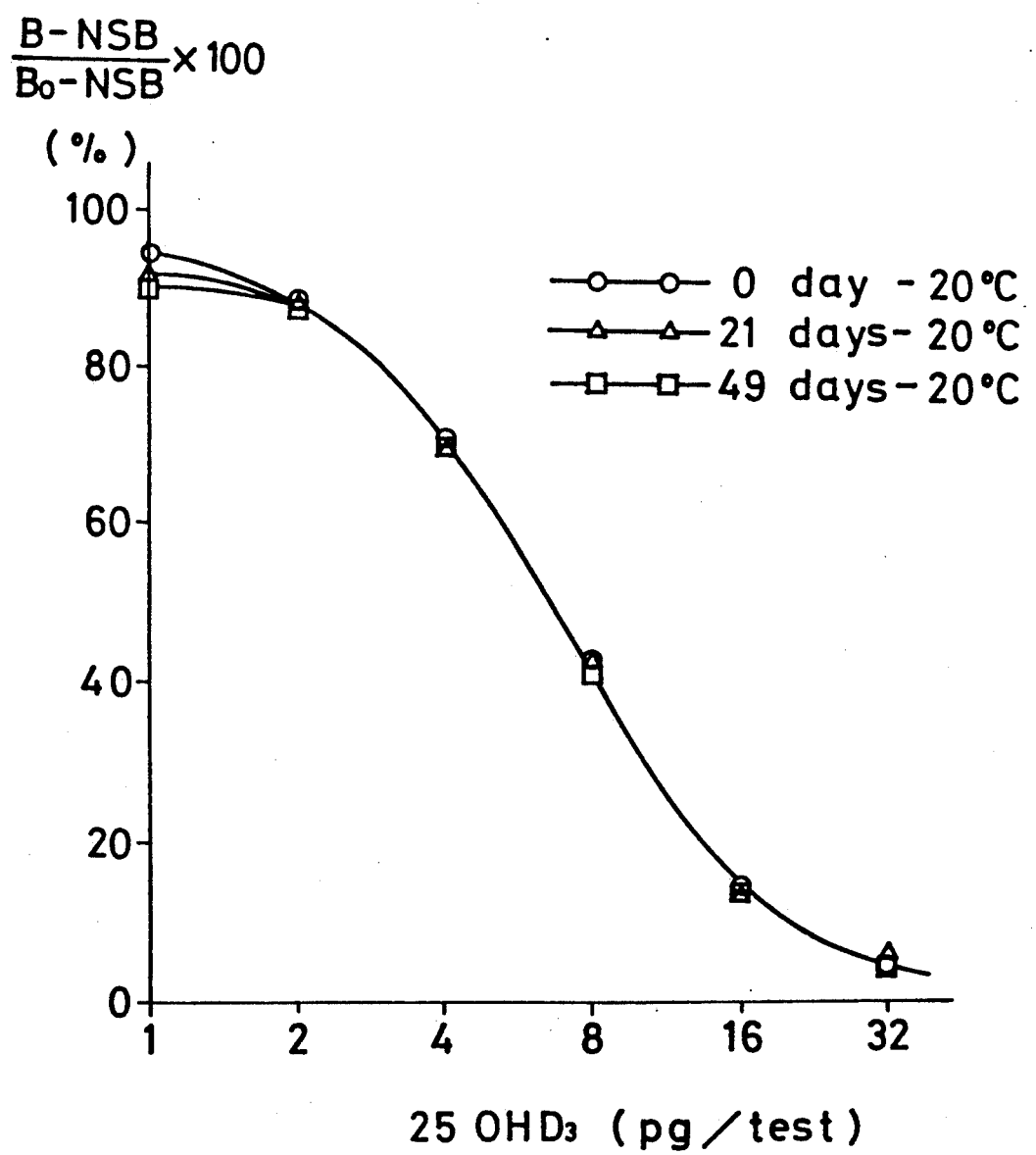

25-HYDROXY VITAMIN $D_3$ DERIVATIVES, PROCESS FOR THEIR PRODUCTION, AND ASSAY METHOD USING THE SAME

This application is a division of application Ser. No. 07/258,017, filed Oct. 14, 1988 now U.S. Pat. No. 5,075,465.

FIELD OF THE INVENTION

This invention relates to novel 25-hydroxy vitamin $D_3$ derivatives, their production and an assay method using the same.

DESCRIPTION OF THE PRIOR ART

For the assay of 25-hydroxy vitamin $D_3$, a competitive protein binding assay (CPBA) method and a radio immunoassay (RIA) method are known. In these methods, a tritium [$^3$H]-labeled compound is used (PCT Open No. 56-500538). An example thereof is a tritium-labeled 25-hydroxy vitamin $D_3$ derivative with position-1 carbon (Japan Pat. Unexam. Publ. No. 60-163859). As the vitamin D binding protein used in the CPBA method, it is also known to use the plasma of rats fed with vitamin D-deficient feed [Vitamin, 55(12), 595–605: 1981]. As haptens for the preparation of antibodies used in the RIA method, substances having carbonyl in a side chain terminal are known. (Japan Pat. Unexam. Publ. Nos. 58-92656, 55-47653 and 59-148775.)

In these assay methods, as the isotopically labeled compound, tritium [$^3$H]-labeled 25-hydroxy vitamin $D_3$ is used.

In the assay of 25-hydroxy vitamin $D_3$ in a specimen, the prior-used tritium [$^3$H]-labeled compounds were of low specific activity as compared with either $^{32}$P or $^{125}$I as to radiation energy and suffered from high cost and involved cumbersome operations.

BRIEF SUMMARY OF THE INVENTION

We have discovered radioisotope iodine-labeled 25-hydroxy vitamin $D_3$ derivatives with high radiation energy and superior characteristics of use.

Heretofore, there have been known isotopically labeled vitamin $D_3$ derivatives with tritium [$^3$H] labeling, which have $\beta$-ray nuclear emission with low radiation energy per unit time.

However, no information was known on $^{125}$I-labeled vitamin $D_3$ derivatives which have $\gamma$-ray nuclear emission with high radiation energy, because the conjugated triene structure of vitamin $D_3$ is unstable and was thought to be subject to auto-degradation by inducing radical reactions.

The $^{125}$I-labeled 25-hydroxy vitamin $D_3$ derivatives of the present invention are, on the contrary, stable without structural degradation by $\gamma$-rays and hence are useful for radio immunoassay.

In radioisotope labeling, direct labeling (chloramin-T method) and indirect labeling (Bolton-Hunter reagent method) are known. (*Amersham Note*, Nov. 1, 1981).

The indirect method under mild reaction conditions is preferable due to the instability of vitamin D in the presence of acid, oxygen, oxidizing agents, heat or light.

We have synthesized novel 25-hydroxy vitamin $D_3$ amino acid derivatives having a terminal amino group in a side chain. The said derivatives as haptens are bound with carrier protein and are inoculated into animals to obtain antibodies. Furthermore, the derivatives are labeled with radioisotope iodine. Using the obtained antibodies and radioisotope iodine-labeled compounds, we have established a radio immunoassay system, then have found that in an assay of 25-hydroxy vitamin $D_3$ in a specimen the said assay system is highly sensitive and useful.

Also in the CPBA method using DBP, radioisotope iodine-labeled compounds of the present invention are found to be useful for assaying 25-hydroxy vitamin $D_3$ with high sensitivity.

OBJECTS OF THE INVENTION

An object of the present invention is to provide novel 25-hydroxy vitamin $D_3$ amino acid derivatives of the formula

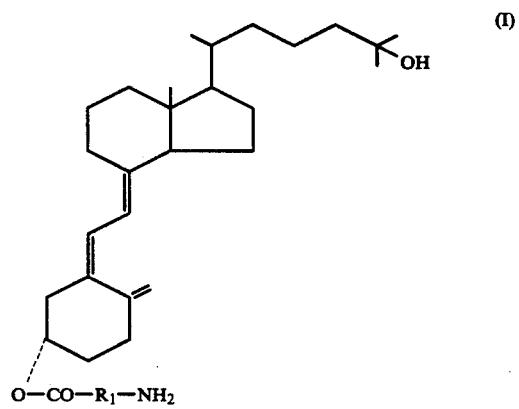

$$\text{O—CO—R}_1\text{—NH}_2 \qquad (I)$$

wherein $R_1$ is $C_{1-10}$ alkylene.

Another object of the present invention is to provide a process for the production of novel 25-hydroxy vitamin $D_3$ amino acid derivatives [I], which comprises removing a protective group for the amino group in 25-hydroxy vitamin $D_3$ derivatives of the formula

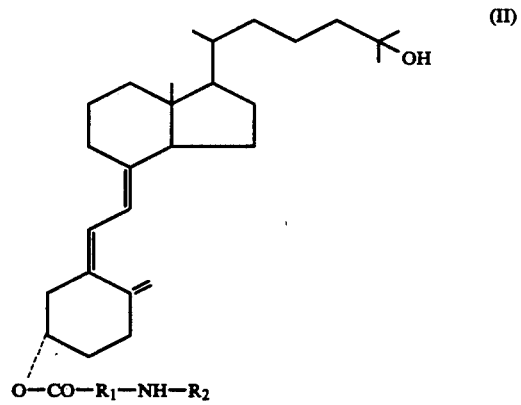

$$\text{O—CO—R}_1\text{—NH—R}_2 \qquad (II)$$

wherein $R_1$ is $C_{1-10}$ alkylene and $R_2$ is a protective group for the amino group, in the presence of a base in an insert solvent.

A further object of the present invention is to provide radioisotope iodine-labeled 25-hydroxy vitamin $D_3$ derivatives of the formula

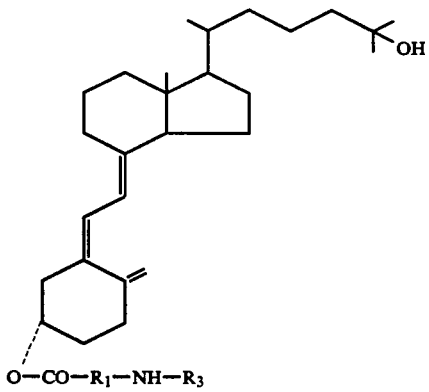

(III)

wherein $R_1$ is $C_{1-10}$ alkylene and $R_3$ is a radioisotope iodine-labeled residue.

A still further object of the present invention is to provide an assay method for 25-hydroxy vitamin $D_3$ in a specimen, which comprises the following steps:

adding to a specimen containing 25-hydroxy vitamin $D_3$ a radioisotope iodine-labeled 25-hydroxy vitamin $D_3$ derivative of formula [III];

adding to the mixture thus formed anti-25-hydroxy vitamin $D_3$ antibody;

separating the thus-generated bound form of radioisotope iodine-labeled 25-hydroxy vitamin $D_3$ derivative-anti 25-hydroxy vitamin $D_3$ antibody and unreacted free form of radioisotope iodine-labeled 25-hydroxy vitamin $D_3$ derivative; and measuring the amount of labeled radioisotope iodine in a bound or free form.

Still another object of the present invention is to provide an assay method for 25-hydroxy vitamin $D_3$ in a specimen, which comprises the following steps:

adding to a specimen containing 25-hydroxy vitamin $D_3$ a radioisotope iodine-labeled 25-hydroxy vitamin $D_3$ derivative of formula [III];

adding to the mixture thus formed vitamin D binding protein (hereinafter designated as DBP);

separating the thus-generated bound form of radioisotope iodine labeled 25-hydroxy vitamin $D_3$ derivative-DBP and unreacted free form of radioisotope iodine labeled 25-hydroxy vitamin $D_3$ derivative; and measuring the amount of labeled radioisotope iodine in a bound of free form.

BRIEF DESCRIPTION OF THE DRAWINGS

In the accompanying drawings:

FIG. 6 is the stability curve of an [$^{125}$I]-labeled 25-hydroxy vitamin $D_3$ derivative by the CPBA method using DBP instead of anti-25-hydroxy vitamin $D_3$ antibodies.

DETAILED DESCRIPTION OF THE INVENTION

Figure 1:
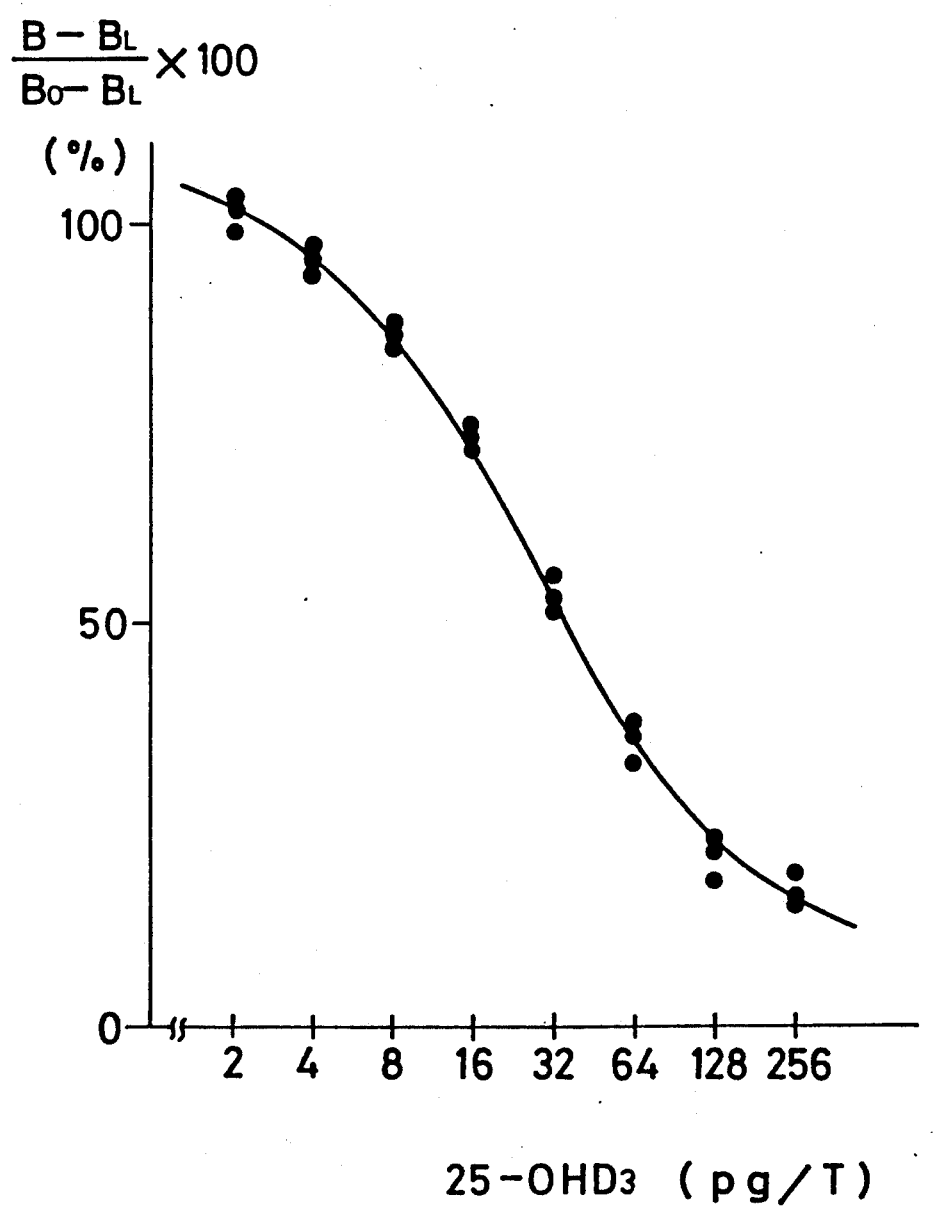
FIG. 1 is the standard curve of an [$^{125}$I]-labeled 25-hydroxy vitamin $D_3$ derivative.

25-Hydroxy vitamin $D_3$ amino acid derivatives of formula [I] can be obtained by covalently bonding an amino acid with the 3$\beta$-hydroxy group of 25-hydroxy vitamin $D_3$. In formula [I], $R_1$ is $C_{1-10}$ alkylene. Compound [I] can be used a derivative of a hapten in the preparation of anti-25-hydroxy vitamin $D_3$ antibodies. The linkage of a hapten derivative and a carrier protein is preferably a 1-10 carbon chain, and more preferably 2-6 carbon, so $R_1$ is more preferably $C_{2-6}$ alkylene.

Compound [I] can be prepared by first reacting 25-hydroxy vitamin $D_3$ with an amino acid having a protected amino group to obtain a 25-hydroxy vitamin $D_3$ derivative [II] and removing the protective group therefrom.

The amino acid is a compound of the formula

$$HOOC-R_1-NH_2 \qquad [IV]$$

wherein $R_1$ has the same meaning as hereinbefore.

Examples of alkylene $R_1$ are n=1; glycine, n=2; $\beta$-alanine, n=3; $\gamma$-amino-butyric acid and $\beta$-amino-isobutyric acid, n=4; $\delta$-amino valeric acid, n=5; $\epsilon$-amino-n-caproic acid, n=6; 7-amino heptanoic acid, and n=10; 11-amino undecanoic acid. The carbon chain in the amino acid is preferably a straight chain and is preferably $C_{2-6}$ alkylene. $\delta$-amino-levulinic acid, glycylglycine or $\delta$-amino acid, i.e. D and/or L-lysine can also be used. An amino acid having side chain hydroxyl, for example 4-amino-3-hydroxybutyric acid can be used if the hydroxyl group is protected.

The protective group for the amino group may be a group which can easily be removed under mild conditions and under weakly basic conditions due to the possible instability of vitamin D under severe removal conditions. Examples are 9-fluorenyl methyloxycarbonyl (hereinafter designated as Fmoc), 9-(2-sulfo)-fluorenyl methyloxycarbonyl, 1,1-dimethyl-2-cyanoethyloxy carbonyl and 5-benzisoxazolyl methyloxycarbonyl. 9-Fluorenyl methyloxycarbonyl is preferred. Amino group protection can be effected by known methods therefor, by reacting an activated derivative, for example an activated ester having Fmoc, such as 9-fluorenyl-methyl-succinimidylcarbonate or 9-fluorenylmethylchloroformate, with an amino acid [L. A. Carpino and G. Y. Ham, J. Org. Chem. 37: 3404 (1972)].

25-hydroxy vitamin $D_3$ amino acid derivatives of formula [II] can be obtained, for example using an Fmoc-amino acid as an amino protected amino acid, by reacting one equivalent of 25-hydroxy vitamin $D_3$ with one equivalent of Fmoc-amino acid or its acid anhydride, acid halide or activated ester to obtain compound [II]. More preferably, one equivalent of Fmoc-amino acid is reacted with one equivalent of mixed anhydride having another acid, under an inert gas, and a base in an anhydrous solvent. The reason for reacting the said mixed anhydride with 25-hydroxy vitamin $D_3$ is to prevent the formation of a by-product, 25-hydroxy vitamin $D_3$ having an Fmoc-amino acid on a hydroxy group at position-25.

Examples of other acids in a mixed anhydride are valeric acid, pivalic acid or isobutylchloroformate. Pivalic acid is preferred. Examples of anhydrous solvents are anhydrous organic solvents such as tetrahydrofuran or dioxane. Examples of bases are preferably dimethylaminopyridine (DMAP) and piperidinopyridine (PPY), which are preferred for the esterification of secondary or tertiary alcohols with stearic hindrance. The preferred inert gases are argon and nitrogen. The reaction proceeds preferably at 0°-20° C. for 1-3 hours. The thus-obtained 25-hydroxy vitamin $D_3$ derivative [II] can be purified, if necessary, by any conventional purification method such as column chromatography or thin layer chromatography (TLC).

The said 25-hydroxy vitamin $D_3$ derivative of formula [II] is subjected to de-protection of the amino group, i.e. removal of Fmoc, in the presence of a base in an inert solvent to produce a 25-hydroxy vitamin $D_3$ derivative of the formula [I]. Examples of bases are piperidine, morpholine or ethanolamine. Morpholine is preferred. Examples of inert solvents are ethanol and methanol, preferably anhydrous ethanol or anhydrous methanol. The reaction proceeds under an inert gas in the dark at 0°-20° C. for 1-3 hours.

The thus-obtained 25-hydroxy vitamin $D_3$ derivative [I] can be purified by column chromatography or TLC.

In a radioisotope iodine-labeled 25-hydroxy vitamin $D_3$ derivative of formula [III], $R_1$ has the same meaning as in formula [I] and $R_3$ is a radioisotope iodine-labeled residue. Examples of radioisotopes of iodine are $^{125}I$ and $^{131}I$. The relatively long-half-life isotope $^{125}I$ is preferred. Examples of radioisotopes of iodine-labeled residues are 3-(4-hydroxy-3-iodo [$^{125}I$] phenyl)-propionyl, 3-(3,5-diiodo $^{125}I$]-4-hydroxyphenyl) propionyl, 2-(4-hydroxy-3-iodo [$^{125}I$]phenyl) acetyl, 2-(3,5-di-iodo [$^{125}I$]-4-hydroxyphenyl) acetyl, 2-iodo [$^{125}I$] acetyl, 4-iodo [$^{125}I$] benzoxymethyl carbonyl and N-substituted-3-iodo [$^{125}I$] tyrosine residue. Among these, 3-(4-hydroxy-3-iodo [$^{125}I$] phenyl) propionyl and 3-(3,5-diiodo [$^{125}I$]-4-hydroxyphenyl propionyl are preferred.

In the production of radioisotope iodine-labeled 25-hydroxy vitamin $D_3$ derivatives, a 25-hydroxy vitamin $D_3$ amino acid derivative [I] is labeled with radioisotope iodine by an indirect labeling method by means of the Bolton-Hunter reagent to obtain a radioisotope iodine-labeled 25-hydroxy vitamin $D_3$ derivative. An indirect labeling method herein is a method for producing radioisotope iodine-labeled 25-hydroxy vitamin $D_3$ derivative [III] by reacting a reactive derivative [IV] hereinbelow, which has a radioisotope iodine-labeled residue, with 25-hydroxy vitamin $D_3$ amino acid derivative [I].

The above reactive derivative [IV] is expressed by the formula

$$R_3-X \qquad [IV]$$

wherein $R_3$ has the same meaning as hereinbefore, and X is succinimidyl-N-oxy, phthalimidyl-N-oxy, 5-norbornene-2,3-dicarboximidyl-N-oxy or maleimidyl-N-oxy. N-succinimidyl-3-(4-hydroxy-3-iodo [$^{125}I$] phenyl) propionate, for which $R_3$ is 3-(4-hydroxy-3-iodo [125] phenyl) propionyl and X is succinylimidyl-N-oxy in the compound [IV], is a commercially available [$^{125}I$] Bolton-Hunter reagent. For example, an indirect labeling method on 25-hydroxy vitamin $D_3$ amino acid derivative [I] using the said Bolton-Hunter reagent can be conducted by reacting several $\mu$ moles to several m mole of radioisotope iodine [$^{125}I$] Bolton-Hunter reagent with a 500-2,000-fold excess amount, preferably 1,000-fold excess amount of 25-hydroxy vitamin $D_3$ amino acid derivative, at 0°-30° C. for 12-72 hours. In order to increase the effect on the RIA or CPBA method, the produced radioisotope-labeled 25-hydroxy vitamin $D_3$ derivative [III] is preferably purified by TLC or HPLC. The thus-obtained $^{125}I$-labeled 25-hydroxy vitamin $D_3$ derivative is stable at $-20°$ C. in ethanol for more than the two month half-life of $^{125}I$, and can be used in radio immunoassays.

The storage temperature is preferably as low as possible, e.g. 5° C.--20° C., but preferably even below $-20°$ C., in alcohol or ether, under an inert gas.

Anti-25-hydroxy vitamin $D_3$ antibodies can be prepared by inoculating a conjugation of a hapten, i.e 25-hydroxy vitamin $D_3$ amino acid derivative [I] and a carrier protein into an animal. Examples of carrier proteins which are essential for obtaining an immunogenic antigen for a hapten, are simple proteins, polypeptides and complex proteins such as glycoproteins. Examples of simple proteins are bovine serum albumin (BSA), human serum albumin or human serum globulin. An examples of a polypeptide is polylysine. An example of a glycoprotein is mucoprotein. Among these, simple proteins are preferred, and bovine serum albumin and human serum albumin are the most preferred.

25-Hydroxy vitamin $D_3$ amino acid derivative [I] and a carrier protein are covalently bonded in the presence of a condensation reagent or crosslinkage reagent. Examples of condensation reagents or crosslinkage reagents are dicyclohexylcarbodiimide (DCC), acid anhydride and glutaraldehyde. DCC is preferred. The conjugation radio of the 25-hydroxy vitamin $D_3$ amino acid derivative and the carrier protein can be, due to the decreasing titer of the antibodies if in excess, 10-40 molecules of 25-hydroxy vitamin $D_3$ amino acid derivative per one molecule of carrier protein.

The thus-prepared conjugate for antibody production is inoculated into an animal to produce antibodies. Inoculation can be by parenteral administration such as subcutaneous or intracutaneous injection. For inoculation, a conjugated antigen of the above 25-hydroxy vitamin $D_3$ amino acid derivative-carrier protein is dissolved in a buffer solution or physiological saline, together with an equal amount of complete Freund's adjuvant (C.F.A.) The mixture is emulsified completely, and inoculated subcutaneously or intracutaneously into a homeothermal animal, about ten times in every 1-3 weeks to immunize the same. Alternatively, the conjugated antigen can be directly inoculated into a spleen. During the immunization period, the serum antibody titer is measured at constant time intervals; and at maximum titer, a whole blood sample is collected and allowed to stand for coagulation. The coagulated sample is centrifugally separated to obtain an antiserum containing anti-25-hydroxy vitamin $D_3$ antibodies.

The type of homeothermal animals is not limited and can be any animal which has antibody production activity. To obtain large amounts of antibodies, sheep or bovines can be used. In general, rabbits or rats are preferred.

The isolation of anti-25-hydroxy vitamin $D_3$ antibody from the antiserum can be performed by any conventional method for antibody purification. For example, ammonium sulfate fractionated antiserum can be treated by ion-exchange chromatography or gel-filtration.

Another method of the production of the antibodies is that spleen cells, which can produce the desired antibodies of the animal, are inoculated with conjugated antigen of 25-hydroxy vitamin $D_3$ amino acid derivative-carrier protein, and are fused with established myeloma cells, and the thus-obtained hybridoma is cultured. Then the monoclonal antibodies produced by the said hybridoma are used.

For example, an emulsion, which is prepared by mixing a conjugated antigen of 25-hydroxy vitamin $D_3$ amino acid derivative-carrier protein dissolved in buffer solution or physiological saline and an equal amount of C.F.A., is inoculated subcutaneously in mice, for example Balb/c for sensitization. Cell-fusion is performed 3-5 days after final sensitization. At 3-5 days after final sensitization, spleen cells which produce anti-25-hydroxy vitamin $D_3$ antibodies are collected and fused with established myeloma cells which can be cultured for a long term. Long-term culturable established cells may be defined as cells which can be cultured and grown for a long term in vitro or in vivo, and which can produce immunoglobulin or its related proteins. Generally, well-grown myeloma cells are used. Preferred examples of myeloma cells are the cell-lines P3-NSI/1-Ag4-1, P3-X63-Ag8U1, SP2/U-Ag14 and MPC11-45.6.TG.1.7. In the present invention, P3-X63-Ag8U1 is preferred. The cells can be cultured in a conventional cell culture medium. For example culture can be performed in a medium of 10% FCS to which is added RPMI 1640 (tradename, Flow Laboratory) to which is added glutamine, pyruvic acid, penicillin and streptomycin. For stock culture, S-azaguanine is added to the above medium. Myeloma cells $1-3 \times 10^8$ cells, are used for cell fusion. Spleen cells can be prepared by cutting mouse spleen and crushing it on a mesh to prepare a spleen cell suspension. Washed cells, generally $1-3 \times 10^8$ cells, are fused with myeloma cells by mixing together. The ratio of mixed cells can be myeloma cells:spleen cells 1:3-10. Cell fusion is achieved in a medium for hybridoma. In the cell fusion, a conventional cell-fusion method using a promoter such as Sendai virus or polyethylene glycol (PEG) is preferred. PEG is particularly preferred.

The fused cells are inoculated into the medium for hybridoma and incubated, then selected by incubating in HAT medium. HAT medium is a medium for hybridoma with added hypoxanthine, aminopterin and thymidine. Since more than two hybridomas can be grown in the well of cell-separation plate, more than two kind of antibodies are possibly produced, or no-antibody producing cells may be a contaminant; so in order to obtain cells having the same properties, each clone should be separated. For cloning, a limiting dilution culture or soft agar culture is used. In this invention, a limiting dilution culture is preferred.

The thus-obtained hybridoma secreting anti-25-hydroxy vitamin $D_3$ antibodies with high titer can be stored after lyophilization at an early stage. Lyophilization can be performed by a conventional method, namely cell suspension in a small tube or ampule with freezing in a $-80°$ C. freezer and storage in liquid nitrogen. Another example of hybridoma production is that the above hybridoma is inoculated intraperioneally in pristan (2,6,10,14-tetramethylpentadecane, Aldrich Chemicals) treated mice, and after about 10 days the ascites are collected. Another method is that the hybridoma is incubated into bovine fetal serum with added RPMI medium or into Darbecco-modified Eagle medium. The antibodies thus obtained can be purified by any conventional method. For example, the antibodies are fractionated with ammonium sulfate and treated by ion-exchange chromatography, gel filtration and affinity chromatography to fractionate IgG. Then purified anti-25-hydroxy vitamin $D_3$ monoclonal antibodies can be obtained.

Furthermore, anti-25-hydroxy vitamin $D_3$ monoclonal antibody-producing cells can b inoculated and grown in an animal having identical histocompatibility antigens or in nude mice as a tumor, and the grown cells are collected and the monoclonal antibodies separated therefrom.

In an assay of 25-hydroxy vitamin $D_3$, anti-25-hydroxy vitamin $D_3$ polyclonal antibodies or anti-25-hydroxy vitamin $D_3$ monoclonal antibodies (hereinafter sometimes collectively designated anti-25-hydroxy vitamin $D_3$ antibody) can be used in its soluble state or in an immobilized state. An insoluble carrier and anti-25-hydroxy vitamin $D_3$ antibodies are bound by using a polyfunctional reagent and the immobilized antibody has antibody titer against 25-hydroxy vitamin $D_3$. Examples of polyfunctional reagents are compounds having more than two groups which can react with functional groups such as amino, hydroxyl, carboxyl and thiol, and comprise aldehydes such as succinaldehyde, glutaraldehyde and adipoaldehyde; dicarboxylates such as malonic acid, succinic acid glutaric acid or adipic acid or their reactive derivatives; diisocyanates such as hexamethylene diisocyanate or 2,4-toluenediisocyanate; diisothiocyanates such as hexamethylene diisothiocyanate; maleimide carboxylates such as maleimide benzoate or maleimide phenylacetate or their functional derivatives; dimaleimides such as N,N-ethylene-bis-maleimide or N,N'-O-phenylene dimaleimide, bisdiazobenzidine, diethylmalonimidate, dimethyladipinimidate or N,N'-polymethylene-bisiodo acetamide and thiocarboxylates such as 3-(2'-benzothiozolyl-dithio) propionate and 3-(2'-pyridyldithio) propionate or their functional derivatives. The polyfunctional reagent can be selected by considering the bonding of functional groups such as amino, carboxyl, hydroxyl or thiol in anti-25-hydroxy vitamin $D_3$ antibody.

The immobilized carrier is a carrier having a reactive group which does not bond with groups for bonding with antibodies in polyfunctional groups. Examples of immobilized carriers are insoluble proteins such as albumin or gelatin; epichlorhydrin-treated insoluble polysaccharides such as agarose, cellulose or dextrin; insoluble polymers or copolymers of acrylonitrile, acrylic acid, acrylate ester, methacrylic acid, methacrylate ester, vinyl alcohol, binyl acetate, styrene, aminostyrene, chlorstyrene, maleic acid and fumaric acid, which is treated with bromocyanate and is introduced with a spacer corresponding to amino group introduction, and an insoluble inorganic carrier which is introduced with a functional group such as an amino group into an inorganic compound such as one of silicon and aluminum. The immobilized carrier may also be a carrier which can bind anti-25-hydroxy vitamin $D_3$ antibodies by physical adsorption.

The immobilized carrier is preferably in particulate form which can be easily isolated by filtration, for example beads having a diameter more than 1 mm and preferably more than 5 mm, or a spindle form which corresponds to the bottom shape of an antigen-antibody reaction tube.

The introduction of reactive group into anti-25-hydroxy vitamin $D_3$ antibodies using a spacer-introducing reagent can be performed by introducing additional functional groups such as aldehyde, carboxyl, amino or thiol, reacting with at least one spacer introducing reagent, for example a dialdehyde such as succinaldehyde, glutaraldehyde or adipoaldehyde; a reactive derivative such as acid chloride, a succinimide ester or p-nitrophenyl ester of ω-amino butyric acid or ω-amino glutamic acid; a reactive derivative of dicarboxylic acids such as malonic acid, succinic acid, glutaric acid or adipic acid; diamines such as hexamethylene diamine or decamethylene diamine; reactive derivatives of 3-(2'-pyridyldithio) propionic acid or 3-(2'-benzothiazolyldithio) propionic acid, S-acetyl-mercapto succinic anhydride or thiols such as 2-aminoethanethiol.

Anti-25-hydroxy vitamin $D_3$ antibodies are condensed directly or through polyfunctional reagents with reactive groups in the immobilized carrier. Condensation reactive process generally at 0°-40° C. in a pH 6.0-8.5 buffer solution or organic solvent or mixture thereof. Furthermore, a second antibody which is obtained by immunizing large mammals inoculated with an immunoglobulin fraction in a serum, which is used for antibody production of 25-hydroxy vitamin $D_3$, is immobilized and anti-25-hydroxy vitamin $D_3$ antibody is bound thereto by an antigen-antibody reaction to prepare the immobilized antibody.

The thus-obtained immobilized antibodies are washed and stored.

In an assay of 25-hydroxy vitamin $D_3$ in a specimen using anti-25-hydroxy vitamin $D_3$ antibodies in a liquid soluble phase, a fixed amount of radioisotope iodine-labeled 25-hydroxy vitamin $D_3$ derivative [III] is first added to a specimen containing 25-hydroxy vitamin $D_3$, then an optimum amount of anti-25-hydroxy vitamin $D_3$ antibodies is added to form an antigen antibodies reaction product.

The thus-formed labeled 25-hydroxy vitamin $D_3$ derivative-anti-25-hydroxy vitamin $D_3$ antibodies binding complex, and the 25-hydroxy vitamin $D_3$-antibodies binding complex, and the free labeled 25-hydroxy vitamin $D_3$ derivative are separated by using specific antibodies for anti-25-hydroxy vitamin $D_3$ antibodies. The said specific antibodies are hereinafter referred to as second antibodies. The second antibodies can be obtained, for example by inoculating a normal immunoglobulin fraction into the serum of an animal which is used for antibodies production of 25-hydroxy vitamin $D_3$, as an antigen to immunize, then isolating the second antibodies from the thus-obtained anti-serum. The second antibodies can be purified if necessary by any known method, or they can preferably be used in the condition of an antiserum.

An assay method for 25-hydroxy vitamin $D_3$ in a specimen using anti-25-hydroxy vitamin $D_3$ antibodies and radioisotope iodine-labeled 25-hydroxy vitamin $D_3$ derivative is illustrated as follows:

25-Hydroxy vitamin $D_3$ in a specimen such as a known serum, is extracted from the serum specimen. A sample, which is a mixture of serum and an equal amount of added solvent, is stirred allowed to stand and centrifuged. The separated supernatant solution is treated by column chromatography and a fraction of 25-hydroxy vitamin $D_3$ is collected and preferably is purified by HPLC.

The 25-hydroxy vitamin $D_3$ fraction can be checked by previously added tritium [$^3$H]-labeled 25-hydroxy vitamin $D_3$. The 25-hydroxy vitamin $D_3$ fraction is dried in vacuo, flushed with argon gas and dissolved in ethanol to prepare a specimen. A fixed amount of radioisotope iodine-labeled 25-hydroxy vitamin $D_3$ derivative is added to the specimen, and the most suitable amount of anti-25-hydroxy vitamin $D_3$ antibody is added thereto. The mixture is incubated in a medium for antigen-antibodies such as a phosphate buffer or a veronal buffer at 4°-5° C. for about 15-72 hours to promote the competitive reaction of radioisotope iodine-labeled hapten and non-labeled hapten to antibodies. The thus-formed antigen antibody binding complex, namely a bound form of radioisotope iodine-labeled 25-hydroxy vitamin $D_3$ derivative-anti-25-hydroxy vitamin $D_3$ antibody (B) and an unreacted free form of radioisotope iodine-labeled 25-hydroxy vitamin $D_3$ derivative (F) are separated by the dextran-charcoal (DC) method by filtration or by centrifugation at 3,000 r.p.m. for 15 mins. Upon B-F separation, the radioactivity of each of B and F is measured.

The amount of 25-hydroxy vitamin $D_3$ (H) in a specimen is calculated by measuring the radioactivity $B/(B+F)$ or $B/F$. Namely, when the amount of H is increased, the radioactivity of B is decreased and that of F is increased. Therefore, the unknown amount of H can be determined by measuring the radioactivity of B and F from a previously plotted standard curve of known amounts.

Upon B-F separation, when the double antibody technique is used with soluble state antibodies, second antibodies, preferably second antibodies containing an antiserum and if necessary a normal serum of the same kind of animal used for anti-25-hydroxy vitamin $D_3$ antibodies production, are added after the competitive reaction and incubated for 1-12 hours. Thereafter the formed binding complex is precipitated by centrifugation at 3,000 r.p.m. for 10-30 mins. to separate precipitate (B) and supernatant (F), then the radioactivity of B or F is measured.

According to the present assay method, a standard curve for 2 pg/Test-256 pg/Test can be prepared, and a rapid reaction time of 16 hours at 5° C. or 1 hour at 37° C. can be achieved. Furthermore, the operation after the reaction is quite simple. Moreover, dilution and recovery tests using the specimens display linearity with high precision. The correlation coefficient between the [$^{125}$I] RIA method of the present invention and the known [$^3$H] CPBA method upon assay of 25-hydroxy vitamin $D_3$ in human serum is correlation coefficient $\gamma=0.980$ ($y=0.928X+1.90$, $n=18$).

Also when antibodies are replaced by known DBP, it can be reacted with a radioisotope iodine [$^{125}$I]-labeled 25-hydroxy vitamin $D_3$ derivative and a standard curve for the range 1-32 pg/Test can be prepared. The DBP can be obtained from the serum of chickens, rats, mice, rabbits, goats, sheep, bovines or humans.

The following examples illustrate the present invention but are not to be construed as limiting:

REFERENTIAL EXAMPLE 1

Extraction and purification of 25-hydroxy vitamin $D_3$ in serum

A mixture of serum 0.5 ml and acetonitrile 0.5 ml was stirred in a BORTEX miser and then allowed to stand for 30 mins. The supernatant solution (0.8 ml) obtained by centrifugation at 3,000 r.p.m. for 10 mins. was charged on a Sept-pack C-18 cartridge column (tradename, MILLIPORE, Waters Corp.) which was activated with ethanol and equilibrated with 50% acetonitrile, and eluted with hydrated acetonitrile. The column was further washed with 50% acetonitrile (4 ml) then eluted with 64% acetonitrile (4 ml) (a fraction of 1α,25-dihydroxy vitamin $D_3$), and eluted with 73% acetonitrile (4 ml) (a fraction of 25-hydroxy vitamin $D_3$ and 24,25-dihydroxy-vitamin $D_3$). The fraction eluted with 73% acetonitrile was dried in vacuo and flushed with argon gas to obtain a fraction containing 25-hydroxy vitamin $D_3$. The thus-obtained crude fraction was dissolved in a mixture (200 μl) of n-hexane-isopropanol (9:1) and purified by HPLC in a Zorbax-SIL (Dupont Inc.) 0.46×25 cm column. The above fractions of 25-hydroxy vitamin $D_3$ was checked by previously added tritium [$^3$H]-labeled 25-hydroxy vitamin $D_3$ [26,27-methyl-$^3$H]. The fraction of 25-hydroxy vitamin $D_3$ (Rt=4-5 mins.) was dried in vacuo and flushed with argon gas.

The said fractions were dissolved in ethanol (2 ml) and 20 μl thereof was used for an assay.

The recovery of 25-hydroxy vitamin $D_3$ was 94.6 ±2.4% (n=18).

REFERENTIAL EXAMPLE 2

3-(N-fluorenyl methyloxy carbonyl) amino propionic acid

γ-amino-n-propionic acid (178 mg, 2 mM) was added to N-succinimidyl-9-fluorenylmethyloxycarboxylate (674 mg, 2 mM) dissolved in a mixture of tetrahydrofuran (THF)-dimethylformamide (DMF)-$H_2O$ (1:2:2) (25 ml) and the mixture was reacted at room temperature overnight. The reaction solvent was distilled off in vacuo and the residue was charged on a column of silica gel (Wako-gel C-200, 75 g) and separated and purified by eluting with $CHCl_3$:methanol=9:1 to obtain the above compound (538.8 mg) (yield: 86.5%).

NMR. δ (DMSO-d6)
2.50-2.60 (2H, t, —$CH_2$—Co—)
3.28-3.35 (2H, m, —$CH_2$—N—)
4.33-4.44 (3H, m, Fmoc)
7.35-8.06 (8H, m, Fmoc)

EXAMPLE 1

25-hydroxy vitamin $D_3$—3β—O—3 8 3'-(N-9-fluorenylmethyloxy carbonyl) aminopropionate]

Pivaloyl chloride (7.38 μl, d=0.979, 0.06 mM) and dimethylamino pyridine (DMAP, 7.32 mg, 0.06 mM) were added to 3-(N-9-fluorenyl methyloxy carbonyl) amino propionic acid (18.7 mg, 0.06 mM) dissolved in dry THF (3 ml), and the mixture was reacted at −15° C. for 15 mins. under an argon atmosphere in the dark. A THF solution (1 ml) of 25-hydroxy vitamin $D_3$ (24.0 mg, 0.06 mM) was added thereto and the mixture was reacted at 0° C. for 1 hour and at room temperature for 1 hour, whereupon 25-hydroxy vitamin D3 disappeared. Methanol (0.5 ml) was added to the mixture to stop the reaction, then distilled off in vacuo. The residue was purified by preparative TLC [Art. 5717, Merck, 20×20 cm, developer: ethylacetate-hexane (1:2)] to obtain the compound (30.1 mg) (yield: 72.4%).

NMR. δ ($CDCl_3$) ppm
0.537 (3H, s, $CH_3$—18)
3.30-3.60 (2H, m, —$CH_2$—N—)
4.10-4.50 (3H, m, Fmoc)
4.80-5.60 (4H, m, H—19E, H—3α, H—19Z, —NH)
5.94-6.29 (2H, m, H—7, H—6)
7.20-7.81 (8H, m, Fmoc)
UV.

$\lambda^{EtOH}_{max}$ nm 300.2, 266.4, 214.4

EXAMPLE 2

25-hydroxy vitamin $D_3$—3β—O—(3-aminopropionate)

25-Hydroxy vitamin $D_3$—3β—O—[3-(N-9'-fluorenyl methyloxy carbonyl) aminopropionate] (30.1 mg, 0.043 mM) obtained in Example 1 was dissolved in ethanol (1 ml). Morpholine (10 ml) was added thereto and the mixture was stirred at room temperature for 1 hour, under an argon atmosphere in the dark, to complete the reaction. The reaction mixture was concentrated in vacuo and purified by preparative TLC [Art. 5717, Merck, 10×20 cm, developer: ethyl acetate-MeOH (1:4)] to obtain the compound (8.3 mg) (yield: 40.6%).

Ninhydrin colorization: positive
NMR. δ ($CDCl_3$) ppm
0.54 (3H, s, $CH_3$—18)
2.36-2.52 (2H, m, —CO—$CH_2$—)
2.90-3.05 (2H, m, —$CH_2$—N—)
3.50-4.00 (2H, b, —$NH_2$)
4.86-5.08 (3H, m, H—19E, H—3α, H—19Z)
5.90-6.30 (2H, m, H—7, H—6)
UV.

$\lambda^{EtOH}_{max}$ nm 264.5

EXAMPLE 3

25-hydroxy vitamin $D_3$—3β—O—[3-(BSA-amino) propionate] antigen and 25-hydroxy vitamin $D_3$ antiserum (1) Preparation of 25-hydroxy vitamin $D_3$—3-β—O—[3-(BSA-amino) propionate] antigen 25-Hydroxy vitamin $D_3$—3β—O—[3-aminopropionate (18.1 mg, 38.43×10$^{-3}$ mM) obtained in Example 2 was dissolved in THF (1 ml), and was added to BSA (M.W. 65,000, 50 mg, 1/50×38.43×10$^{-3}$ mM) dissolved in tris buffer (0.1 M, pH 8.6) at 0° C. with 1-ethyl-3-(3-dimethylaminopropyl)carbodoo,ode hydrochloride (9.6 mg, 1.3×38.43×10$^{-3}$ mM). Chloroform (10 ml) was added four times to the reaction mixture and unreacted 25-hydroxy vitamin $D_3$—3β—O—(3-aminopropionate ester) was removed. The aqueous layer was freeze dried to obtain the lyophilized product (45 mg) which was a complex of 22 molecules of 25-hydroxy vitamin $D_3$—3β—O—(3-aminopropionate ester) bound through an amino group at position-3 thereof to one molecule of BSA.

(2) Preparation of 25-hydroxy vitamin $D_3$ antiserum

The lyophilized 25-hydroxy vitamin $D_3$—3-β—O—[3-(BSA-amino) propionate] (antigen) obtained in (1) above was dissolved in tris buffer (0.1 M, pH 8.6). An equal amount of C.F.a. was added thereto and the material was mixed to emulsify it so as to prepare antigen 1 μg-200 μg/ml. The emulsion was inoculated subcutaneously ten times each two weeks, 50 γ-500γ/head, into rabbits. During this immunization, the titer of blood samples collected every ten days was measured and at maximum antibody titer the whole blood was collected. The blood samples were allowed to stand at room temperature for 60 mins. to coagulate and were centrifuged at 3,000 r.p.m. for 10 mins. to obtain an antiserum containing anti-25-hydroxy vitamin $D_3$ antibodies, which was fractionated with ammonium sulfate to collect an IgG fraction.

(3) Preparation of anti-25-hydroxy vitamin $D_3$ monoclonal antibodies

Lyophilized 25-hydroxy vitamin $D_3$—$3\beta$—O—[3-(BSA-amino) propionate] (antigen) obtained in (1) above dissolved in phosphate buffer, pH 7.2, (50 $\gamma$) together with C.F.A. was inoculated subcutaneously into Balb/c mice, female, 4 weeks age. After 1 week, 50 $\gamma$ thereof was subcutaneously inoculated and after 2 weeks 50 $\gamma$ of antigen was intraperitoneally inoculated. Three days after the final inoculation, their spleens were finely cut and crushed on a mesh to prepare a spleen cell suspension. Cell fusion was performed using mouse myeloma cells P3-X-3-Ag8U1 by a conventional method. 30% PEG (M.W. 1,000) aqueous solution was incubated at 37° C. The spleen cells hereinabove and myeloma cells (total $4 \times 10^7$ cells, 5:1) were suspended in RPMI medium (5 ml) and both cells were gently mixed, centrifuged at 1,000 r.p.m. for 10 mins., then the supernatant was vacuum filtered. The test tube was gently shaken to mix the cell pellets and PEG solution (10 ml) was slowly added and the mixture was gently stirred. The mixture was incubated at 37° C. with gentle shaking, then the fusion reaction was stopped by adding slowly a conventional medium (10 ml) and again the cells were suspended. The suspension was centrifuged at 1,000 r.p.m. for 5 mins. The precipitated cell pellet was dispersed by gently shaking and slowly suspended in HAT medium (5 ml) and was transferred into HAT medium (1 ml) in a vessel. The cells were observed microscopically. The cell suspension was pipetted (each 200 $\mu$l ) into wells in a 96-well plate and grown in a $CO_2$-incubator. The fused cells were selected in HAT medium for cloning by the limiting dilution technique. The obtained clone suspension was grown in the peritonea of pristan-treated Balb/c mice. The IgG fraction was collected by a conventional method from ascites and serum and purified by affinity chromatography using protein A-bound Sepharose CL-4B. The thus-obtained IgG subclass was IgG 1 which was used as monoclonal antibodies.

EXAMPLE 4

Preparation of radioisotope monoiodine [$^{125}$I]-labeled 25-hydroxy vitamin $D_3$ derivative; 25-hydroxy vitamin $D_3$—$3\beta$—O—{3-[N-3-(4-hydroxy-3-iodo [$^{125}$I] phenyl) propionyl] amino propionate}

Iodine [$^{125}$I] Bolton-Hunter reagent [NEN, NEX-120-10, 2,200 Ci/mM, Total 0.33 mCi/100 $\mu$l benzene solution] (100 pM/66.6 $\mu$l/220 $\mu$Ci) and DMAP (1 nM/1 $\mu$l THF) were added to the THF solution (130 $\mu$l) of 25-hydroxy vitamin $D_3$—$3\beta$—O—(3-aminopropionate) (100 nM/127.8 $\mu$l THF) obtained in Example 2, and the mixture was reacted at room temperature for 24 hours under an argon atmosphere in the dark. The reaction mixture was purified by HPLC (Zorbax-SIL, 4.6 mm $\times$ 25 cm column 20% isopropanol-n-hexane, flow 1 ml/min.) The compound hereinabove has Rt=8.50–9.50 min. and recovery 20.0%. (Iodine [$^{125}$I] Bolton-Hunter reagent: Rt=14.0–16.0 min.) Radioisotope monoiodine-labeled 25-hydroxy vitamin $D_3$ was identified with synthesized non-radioisotope monoiodine-labeled 25-hydroxy vitamin $D_3$ by HPLC.

EXAMPLE 5

Preparation of radioisotope diiodine [$^{125}$I]-labeled 25-hydroxy vitamin $D_3$ derivative; 25-hydroxy vitamin $D_3$—$3\beta$—O—{3-[N-3,5-diiodo-4-hydroxy [$^{125}$I] phenyl)propionyl] amino propionate}

Iodine $^{125}$I] Bolton-Hunter reagent [NEN, NEX-120H-10, 4400 Ci/mM, Total 0.33 mCi/100 $\mu$l benzene solution] (25 pM/33.3 $\mu$l/110 $\mu$Ci) and DMAP (1 nM/1 $\mu$l THF) were added to THF solution (120 $\mu$l) of 25-hydroxy vitamin $D_3$—$3\beta$—O—(3-aminopropionate) (25 nM/6.952 $\mu$l THF) obtained in Example 2, and the mixture was reacted at room temperature for 20 hours under an argon atmosphere in the dark. The reaction mixture was purified by HPLC (Zorbax-SIL, 4.6 mm $\times$ 25 cm column, 20% isopropanol-n-hexane, flow 1 ml/min.) The compound hereinabove has Rt=8.90–10.10 min. and recovery 9.9%. (Iodine $^{125}$I] Bolton-Hunter reagent: Rt=14.0–16.0 min.) Radioisotope diiodine-labeled 25-hydroxy vitamin $D_3$ was identified with synthesized non-radioisotope diiodine labeled 25-hydroxy vitamin $D_3$ by HPLC.

EXAMPLE 6

Evaluation of radioisotope iodine [$^{125}$I]-labeled 25-hydroxy vitamin $D_3$ derivative (1) Preparation of Standard Curve Uing Rradio Immunoassay of 25-Hydroxy Vitamin $D_3$ A standard ethanol solution of 25-hydroxy vitamin $D_3$ (256 pg/20 $\mu$l) was diluted stepwise by two-fold dilution to prepare 128 pg/20 $\mu$l, 64 pg/$\mu$l, 32 pg/20 $\mu$l, 16 pg/20 $\mu$l, 8 pg/20 $\mu$l, 4 pg/20 $\mu$l and 2 pg/20 $\mu$l samples.

Samples (20 $\mu$l) of each concentration hereinabove were pipetted into three tubes. Ethanol solutions, each 20 $\mu$l, of radioisotope iodine [$^{125}$I]-labeled 25-hydroxy vitamin $D_3$ derivative which contains as an antioxidant tocopherol was pipetted into each tube (20 $\mu$l, ca. 13,000 cpm).

Anti-25-hydroxy vitamin $D_3$ rabbit serum diluted with tris buffer (approx. 15,000 dilution) pH 8.6, each 1 ml, was added to each tube. Each mixture in the tubes was stirred in a BORTEX mixer and allowed to stand at 5° C. overnight (20–24 hours). Glycine buffer (pH 8.6) suspending a mixture of dextran (T70) and active charcoal (1:10), each 300 $\mu$l) was added into the reaction tubes, and each was stirred by a BORTEX mixer and incubated at 5° C. for 1 hour. B-F separation was performed by centrifugation at 3,000 r.p.m. for 10 mins., and each supernatant solution (1 ml) was measured by an Autowell $\gamma$-counter for 1 min. The ratio of binding is calculated by the following equation:

$$\text{Binding ratio} = \frac{(B) - (BL)}{(Bo) - (BL)} \times 100$$

wherein (B) is the count number in each tube, (BL) is the count number measured by using 25-hydroxy vitamin $D_3$ (1,000 pg/20 $\mu$l) in place of isotope $^{125}$I-labeled 25-hydroxy vitamin $D_3$ derivative, and (Bo) is the count number measured by using 25-hydroxy vitamin $D_3$ at zero concentration. FIG. 1 shows the standard curve of [$^{125}$I]-labeled 25-hydroxy vitamin $D_3$ derivative.

(2) Comparison between tritium [$^3$H]-labeled and [$^{125}$I]-labeled 25-hydroxy vitamin $D_3$ derivative A standard curve was prepared by using tritium [$^3$H]-labeled 25-hydroxy vitamin $D_3$ derivative (26, 27-methyl-$^3$H) as in the case of the [$^{125}$I]-labeled derivative in (1) hereinabove.

Figure 2:
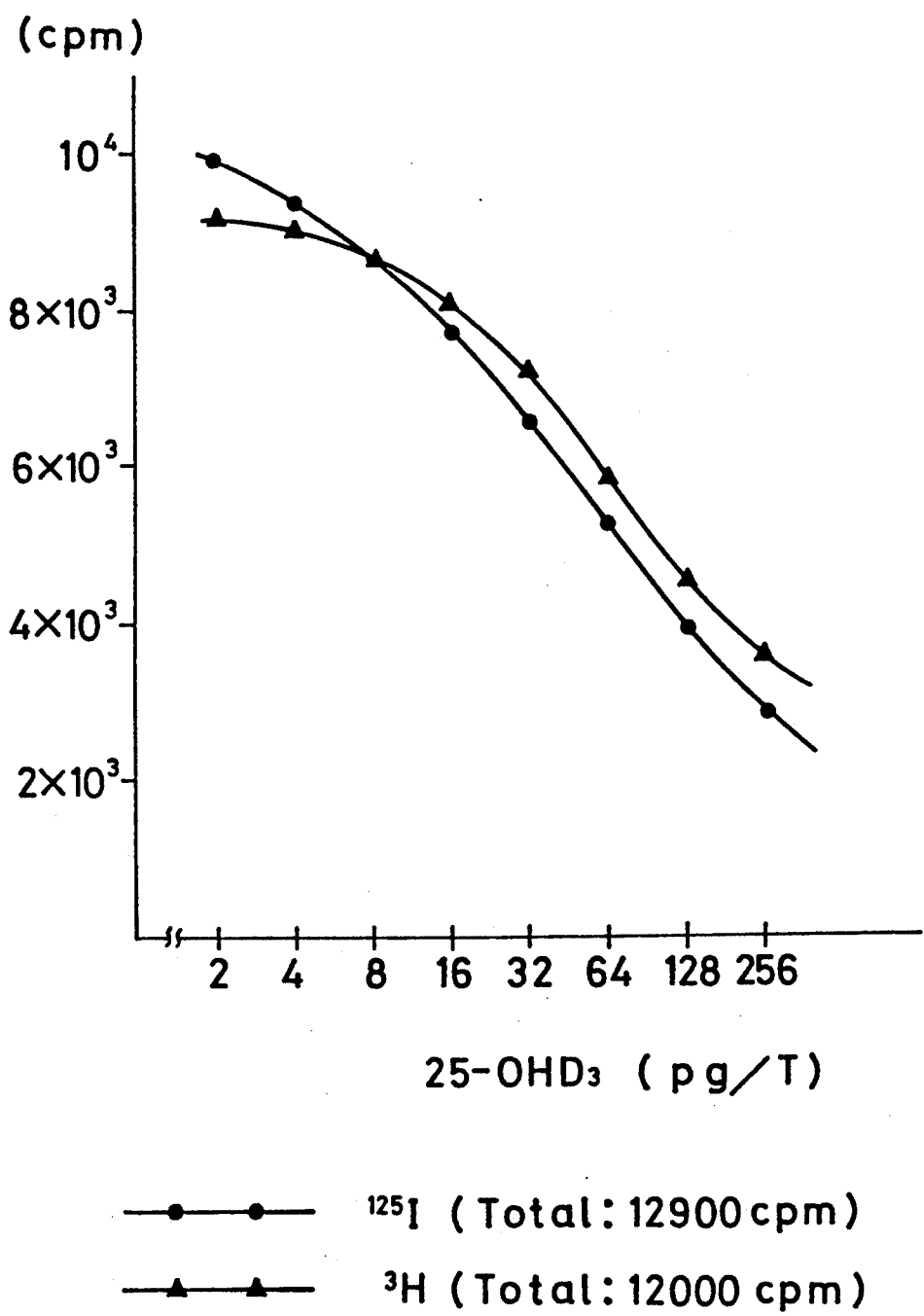
FIG. 2 is the standard curve of an [$^{125}$I]- or [$^3$H]- labeled 25-hydroxy vitamin $D_3$ derivative.

The results are shown in FIG. 2. In FIG. 2, —●—●—: [$^{125}$I]-labeled and —▲—▲—: [$^3$H]-labeled compounds were used. Equal or higher sensitivity was found when using [$^{125}$I] labeling as compared with [$^3$H] labeling, especially at low concentrations (10 pg/Tube), and higher sensitivity was observed.

Figure 3:
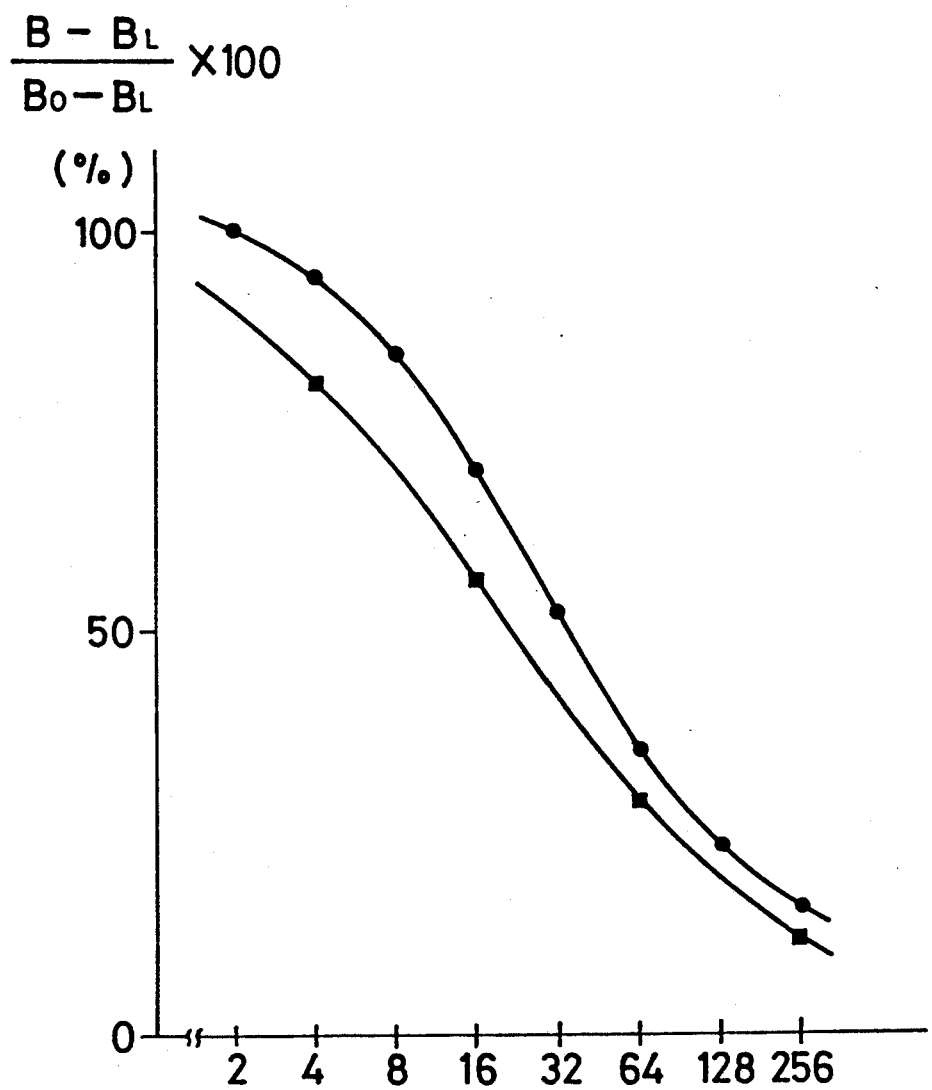
FIG. 3 is the standard curve of a monoiodo [$^{125}$I]- or diiodo [$^{125}$I]-labeled 25-hydroxy vitamin $D_3$ derivative.
Figure 3:
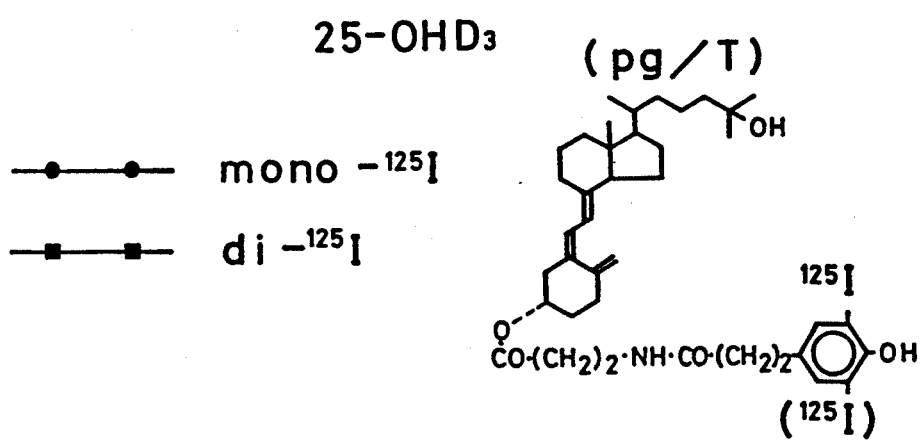

(3) Comparison Between Monoiodine [$^{125}$I] Labeling and Diiodine [$^{125}$I] Labeling Monoiodine [$^{125}$I] labeling and diiodine [$^{125}$I] labeling were compared according to the same method as hereinabove. The results are shown in FIG. 3. In FIG. 3, —●—●— indicates monoiodine [$^{125}$I] labeling, and —■—■— indicates diiodine [$^{125}$I] labeling.

A radioisotope iodine-labeled 25-hydroxy vitamin $D_3$ derivative is illustrated in formula [V]

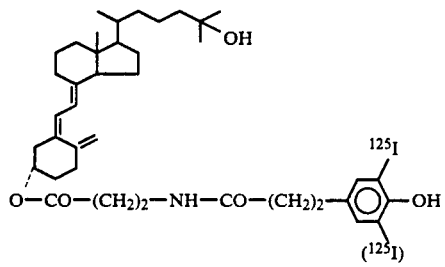

Assays using monoiodine [$^{125}$I]-labeled compound and diiodine [$^{125}$I]-labeled compound show almost the same sensitivity, but monoiodine [$^{125}$I] labeling is preferred.

(4) Comparison with Methylene Chain Length in $R_1$

In formula [IV], assays using compounds having methylene $R_1$ [—$CH_2$)n—] wherein n=1, n=2 and n=3, are compared with each other.

Figure 4:
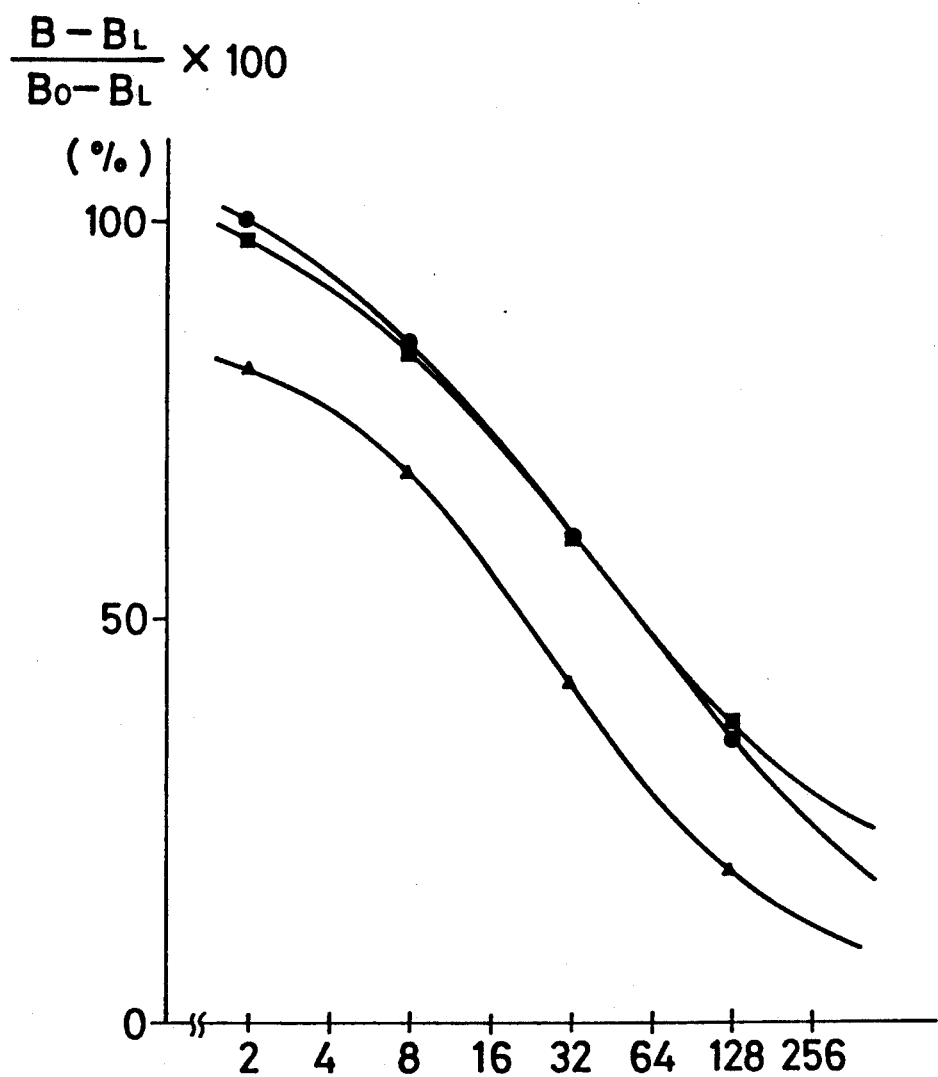
FIG. 4 is the standard curve of compound [IV] wherein $R_1$ is [—$(CH_2)n$—] and n=1, n=2 and n=3.
Figure 4:
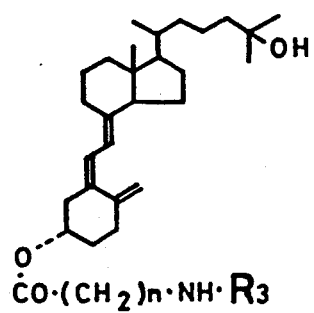

The results are shown in FIG. 4, in which —▲—▲— indicates n=1, —●—●—indicates n=2 and —■—■— indicates n=3. It will be seen that n=2 and n=3 show good results as compared with n=1. Particularly preferred is n=2.

EXAMPLE 7

Evaluation of Radioisotope Iodine-Labeled 25-Hydroxy Vitamin $D_3$ by the CPBA Method Using DBP in Place of Anti-25-Hydroxy Vitamin $D_3$ Antibodies (1) Preparation of DBP Fetal calf serum (FCS) (3.3 ml) diluted with phosphate buffer (pH 7.4, 0.01M) was charged on a column of Blue-Sepharose (tradename Pharmacia Corp. $\phi$2.5×7.5 cm) and a de-albumination treatment through a gel-bed volume of 40 ml was performed.

Fractions, each 5 ml, Nos. 7-10, with absorption at 280 nm, were collected (total 20 ml). Alternatively, FCS can be replaced by the serum of homeothermal animals.

(2) The Standard Curve of Radioisotope Iodine [$^{125}$I]-Labeled 25-Hydroxy Vitamin $D_3$ by the CPBA Method Using DBP, Instead of Antibodies, is Plotted as Follows:

A standard ethanol solution of 25-hydroxy vitamin $D_3$ (1,024 pg/20 μl) was diluted stepwise by two-fold dilutions to prepare 32 pg/20 μl, 16 pg/20 μl, 8 pg/20 μl, 4 pg/20 μl, 2 pg/20 μl and 1 pg/20 μl.

Samples (20 μl) of each concentration hereinabove were pipetted into two tubes. Aliquots of an ethanol solution, each 20 μl, of radioisotope iodine [125I]-labeled 25-hydroxy vitamin $D_3$ derivative, containing as an antioxidant tocopherol, were pipetted into each tube (20 μl, ca. 30,000 cpm) DBP diluted with tris buffer, pH 8.6 (approx. 500-1,000 dilution of DBP fraction in (1) hereinabove) each 500 μl, was stirred and allowed to stand at 4° C. for 16 hours.

Figure 5:
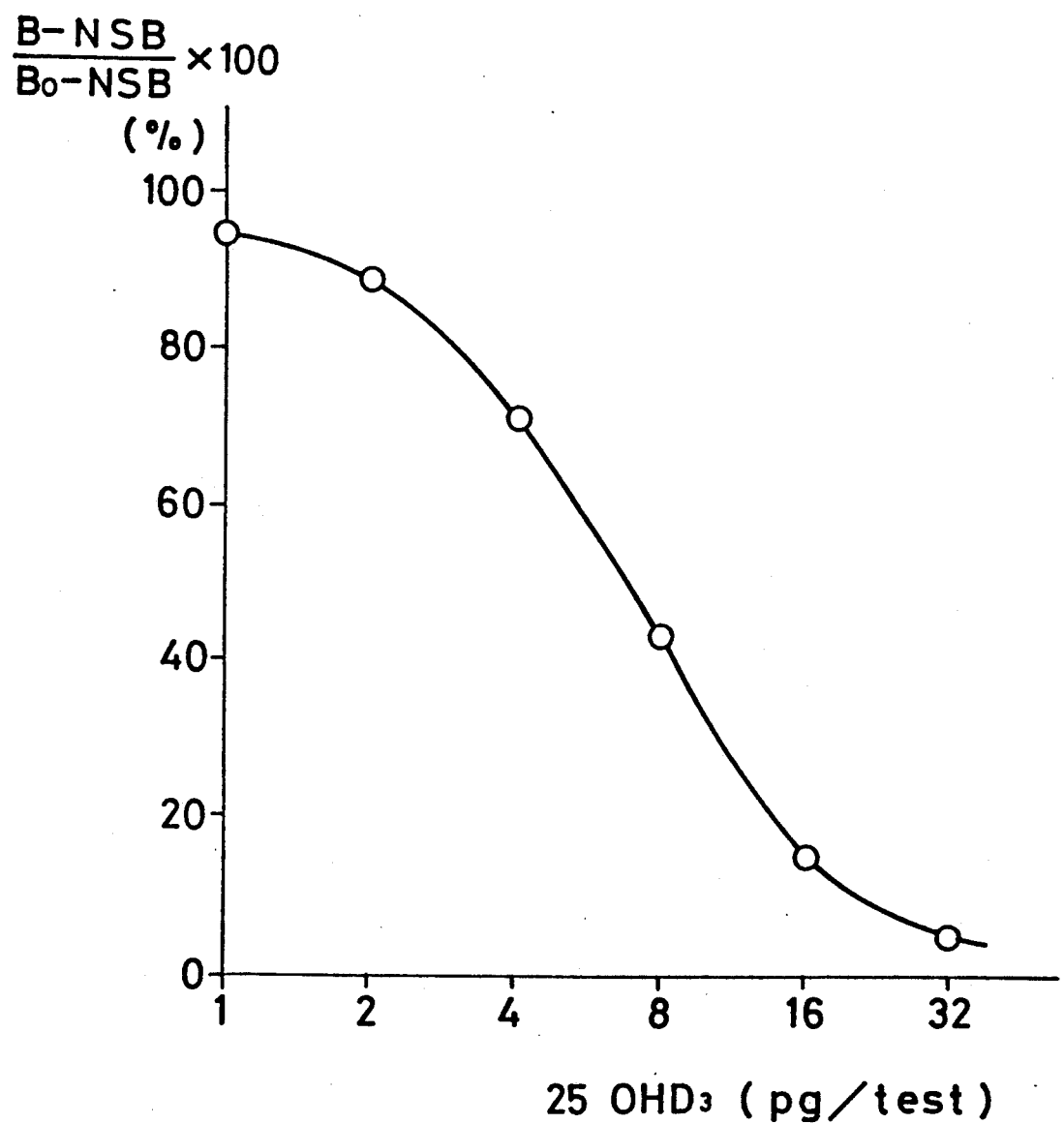
FIG. 5 is the standard curve of an [$^{125}$I]-labeled 25-hydroxy vitamin $D_3$ derivative by the CPBA method using DBP instead of anti-25-hydroxy vitamin $D_3$ antibodies.

Glycine buffer, pH 8.6, suspending a mixture of dextran (T70) and active charcoal (1:10) (each 30 μl), was added into the reaction tubes, stirred and incubated at 4° C. for 30 mins. B-F separation was made by centrifugation at 3,000 r.p.m. for 10 mins. at 4° C., and each supernatant solution 500 μl was measured by an Autowell γ-counter for 1 min. The ratio of binding is calculated by the following equation:

$$\text{Binding ratio} = \frac{(B) - (NSB)}{(Bo) - (NSB)} \times 100$$

wherein (B) is the count number in each tube, (NSB) is the count number measured by using 25-hydroxy vitamin $D_3$ (1,024 pg/20 μl) instead of $^{125}$I-labeled 25-hydroxy vitamin $D_3$ derivative and (Bo) is the count number measured by using 25-hydroxy vitamin $D_3$ at zero concentration. FIG. 5 shows the standard curve of [$^{125}$I]-labeled 25-hydroxy vitamin $D_3$ derivative.

(3) Stability of Radioisotope Iodine [$^{125}$I]-Labeled 25-Hydroxy Vitamin $D_3$ Derivative A 50% $H_2O$-ethanol solution of [$^{125}$I] 25-hydroxy vitamin $D_3$ derivative obtained in Example 4 or Example 5 was stored at −20° C., in an argon atmosphere in a vial. A standard curve using the above sample was prepared according to method (2) hereinabove. In FIG. 6, —○—○— indicates day 0, —△—△— indicating day 21 and —□—□— indicating day 49 of the standard curve are shown. As is shown in FIG. 6, when the material was stored at −20° C., no changes of the standard curve within a range of 2-32 pg/Test were observed. The results show that the [$^{125}$I] 25-hydroxy vitamin $D_3$ derivative can be used in radio immunoassay with good stability.

It will thus be seen that the present invention provides radioisotope iodine-labeled 25-hydroxy vitamin $D_3$ derivatives with high radiation energy and wide usability, compared to low radiation energy, β-ray emitting tritium [$^3$H]-labeled vitamin $D_3$. It might be though that high radiation energy radioisotope iodine [$^{125}$I] vitamin $D_3$ would degrade automatically due to reaction on the conjugated double bond in the vitamin D structure. But [$^{125}$I]-labeled 25-hydroxy vitamin $D_3$ derivative of the present invention in fact does not autodegrade by γ-rays and is quite stable for use in radio immunoassay.

In general, vitamin $D_3$ is metabolized in vivo in the liver or kidney and is converted to activated vitamin $D_3$. The activated vitamin $D_3$, such as 25-hydroxy vitamin D$_3$, 1α, 25-dihydroxy vitamin D$_3$, 1α-hydroxy vitamin D$_3$ and 1α,24-dihydroxy vitamin D$_3$, is used clinically for the therapy of osteoporosis and osteomalacia. The clinical dose thereof is quite low due to its strong physicological action. The pharmacological activity is correlated to the blood level and tissue level of the drug and hence measurement of the blood level of the drug administered to humans is important from a clinical point of view. Considering the above, the present invention is valuable for the assay of activated vitamin D$_3$ in clinical tests.

What is claimed is:

1. An assay method for 25-hydroxy vitamin D$_3$ in a specimen, which comprises the following steps:

adding to a specimen containing 25-hydroxy vitamin D$_3$ a radioisotope iodine-labeled 25-hydroxy vitamin D$_3$ derivative of the formula

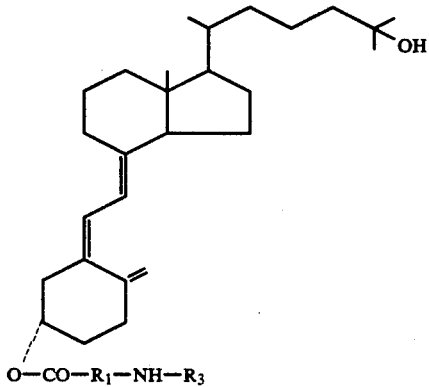

wherein R$_1$ is C$_{1-10}$ alkylene and R$_3$ is a radioisotope iodine labeled residue selected from the group consisting of 3-(4-hydroxy-3-iodo [$^{125}$I] phenyl)-propionyl, 3-(3,5-diiodo [$^{125}$I]-4-hydroxyphenyl) propionyl, 2-(4-hydroxy-3-iodo [$^{125}$I] phenyl) acetyl, 2-(3,5-di-iodo [$^{125}$I]-4-hydroxyphenyl) acetyl, 2-iodo [$^{125}$I] acetyl, 4-iodo [$^{125}$I] benzoxymethyl carbonyl and N-substituted-3-iodo [$^{125}$I] tyrosine residue;

adding to the mixture thus formed an anti-25-hydroxy vitamin D$_3$ antibody;

separating the thus-generated bound form of radioisotope iodine-labeled 25-hydroxy vitamin D$_3$ derivative-anti-25-hydroxy vitamin D$_3$ antibody and unreacted free form of radioisotope iodine-labeled 25-hydroxy vitamin D$_3$ derivative; and measuring the amount of labeled radioisotope iodine in a bound or free form.

2. An assay method for 25-hydroxy vitamin D$_3$ in a specimen, which comprises the following steps:

adding to a specimen containing 25-hydroxy vitamin D$_3$ a radioisotope iodine-labeled 25-hydroxy vitamin D$_3$ derivative of the formula

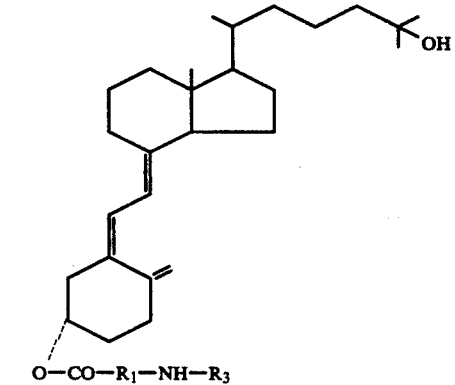

wherein R$_1$ is C$_{1-10}$ alkylene and R$_3$ is a radioisotope iodine labeled residue selected from the group consisting of 3-(4-hydroxy-3-iodo [$^{125}$I] phenyl)propionyl, 3-(3,5-diiodo [$^{125}$I]-4-hydroxyphenyl) propionyl, 2-(4-hydroxy-3-iodo [$^{125}$I] phenyl) acetyl, 2-(3,5-di-iodo [$^{125}$I]-4-hydroxyphenyl) acetyl, 2-iodo [$^{125}$I] acetyl, 4-iodo [$^{125}$I] benzoxymethyl carbonyl and N-substituted-3-iodo [$^{125}$I] tyrosine residue;

adding to the mixture thus formed a vitamin D binding protein (hereinafter designated as DBP);

separating the thus-generated bound form of radioisotope iodine-labeled 25-hydroxy vitamin D$_3$ derivative-DBP and unreacted free form of radioisotope iodine labeled 25-hydroxy vitamin D$_3$ derivative; and measuring the amount of labeled radioisotope iodine in a bound or free form.

3. The method according to claim 1, wherein R$_3$ is 3-(4-hydroxy-3-iodo [$^{125}$I] phenyl) propionyl or 3-(3,5-diiodo [$^{125}$I]-4-hydroxyphenyl propionyl.

4. The method according to claim 2, wherein R$_3$ is 3-(4-hydroxy-3-iodo [$^{125}$I] phenyl) propionyl or 3-(3,5-diiodo [$^{125}$I]-4-hydroxyphenyl propionyl.

* * * * *